United States Patent
Merrill

(10) Patent No.: US 6,960,279 B2
(45) Date of Patent: Nov. 1, 2005

(54) METHOD FOR STABILIZING VINYL AROMATIC MONOMERS USING SELECTED POLYMERIZATION INHIBITORS AND POLYMERS PREPARED THEREWITH

(75) Inventor: James T. Merrill, Katy, TX (US)

(73) Assignee: Fina Technology, Inc., Houston, TX (US)

( * ) Notice: Subject to any disclaimer, the term of this patent is extended or adjusted under 35 U.S.C. 154(b) by 472 days.

(21) Appl. No.: 10/139,524

(22) Filed: May 6, 2002

(65) Prior Publication Data

US 2003/0205452 A1 Nov. 6, 2003

(51) Int. Cl.[7] .............................. B01D 3/34; C07C 7/05; C07C 7/20; C09K 3/00
(52) U.S. Cl. ............................. 203/63; 585/3; 585/802; 585/807; 585/808; 585/809; 585/832; 252/182.18; 252/182.29; 252/404
(58) Field of Search ........................... 585/3, 807, 808, 585/809, 802, 832; 203/63; 252/182.29, 182.18, 404

(56) References Cited

U.S. PATENT DOCUMENTS

| | | | |
|---|---|---|---|
| 4,032,547 A | 6/1977 | Bacha et al. ............. | 260/396 N |
| 4,466,904 A | 8/1984 | Watson et al. ............. | 252/402 |
| 5,583,247 A | 12/1996 | Nesvadba et al. ............. | 560/2 |
| 5,616,774 A | 4/1997 | Evans et al. .................... | 560/4 |
| 5,670,692 A | 9/1997 | Nesvadba et al. ............. | 558/71 |
| 5,750,765 A | 5/1998 | Nesvadba et al. .......... | 560/126 |
| 6,024,894 A | 2/2000 | Arhancet .................... | 252/404 |
| 6,348,598 B1 | 2/2002 | Doi et al. .................... | 546/242 |
| 6,685,823 B2 * | 2/2004 | Benage et al. .......... | 208/48 AA |
| 2004/0010159 A1 * | 1/2004 | Benage ........................ | 558/306 |
| 2004/0034247 A1 * | 2/2004 | Eldin ............................. | 560/4 |

* cited by examiner

Primary Examiner—Joseph D. Anthony
(74) Attorney, Agent, or Firm—Madan, Mossman & Sriram PC; Tenley R. Krueger

(57) ABSTRACT

Disclosed is the observation that 7-aryl-quinone methides and 4-tert-butylcatechol, when used in combination in a vinyl aromatic monomer to inhibit polymerization, do not inhibit polymerization to the same extend as each would if used separately. Stated another way, a phenomenon has been observed that when these two compounds are used together, they can, to a large extent, render each other unable to inhibit polymerization in a vinyl aromatic monomer. Also disclosed are methods of preventing adverse results of this interaction when undesired and a method of using this interaction to prepare a reactive vinyl aromatic monomer having a concentration of 4-tert-butylcatechol that would otherwise inhibit polymerization. The invention is disclosed to be useful with the production and storage of any vinyl aromatic monomer and is disclosed to be particularly useful with the production and storage of styrene monomer.

9 Claims, No Drawings

US 6,960,279 B2

METHOD FOR STABILIZING VINYL AROMATIC MONOMERS USING SELECTED POLYMERIZATION INHIBITORS AND POLYMERS PREPARED THEREWITH

BACKGROUND OF THE INVENTION

1. Field of the Invention

The present invention relates to a method for stabilizing vinyl aromatic monomers using selected polymerization inhibitors and polymers prepared therewith. The present invention particularly relates to a method for stabilizing styrene monomer and polystyrene polymers prepared therewith.

2. Background of the Art

It is well known that vinyl aromatic compounds such as monomeric styrene, alpha-methyl styrene, and the like, polymerize readily and that the rate of such a polymerization increases with increasing temperature. Modern production methods for these and other vinyl aromatic compounds include separation and purification processes. Such separation and purification is often accomplished by distillation.

Various types of polymerization inhibitors have been employed to prevent polymerization during production and storage of vinyl aromatic compounds. For example, U.S. Pat. No. 4,466,904 to Watson, et al., discloses that inhibitors useful for inhibiting the polymerization of vinyl aromatic compounds include 4-tert-butylcatechol(TBC), phenothiazine, and 2,6-dinitro-p-cresol. TBC in particular is a preferred polymerization inhibitor for storage applications, having a good efficiency in preventing premature polymerization and no nitrogen and/or halides that can require special care during waste disposal. Such use of polymerization inhibitors to prevent polymerization of vinyl aromatic monomers is often referred to as stabilization and a monomer having an effective amount of a polymerization inhibitor present is referred to as being stabilized.

Some polymerization inhibitors work well in the absence of oxygen. 2,6-dinitro-p-cresolworks well as a polymerization inhibitor in a vinyl aromatic monomer in an oxygen free process. Others do not. Another class of chemical compounds that is useful as polymerization inhibitors in the production of vinyl aromatic monomers is the phenylenediamines. Certain polymerization inhibitors, such as phenylenediamine and TBC, require the presence of oxygen to inhibit polymerization of vinyl aromatic monomers.

A more recent class of inhibitors, described as 7-substututed quinone methides, has been disclosed in U.S. Pat. No. 5,750,765 to Nesvadba, et al., and U.S. Pat. No. 6,024,894 to Arhancet, et al. In Nesvadba, these polymerization inhibitors are disclosed to be more active than earlier described methides. In Arhancet, the 7-substututed quinone methides are disclosed as being particularly useful when used in combination with N,N-bis(hydroxypropyl)hydroxylamine.

The use of such polymerization inhibitors in general, and TBC in particular, is not trouble free. For example, for many applications, TBC must be removed prior to polymerization of vinyl aromatic monomers. One method of removing TBC from vinyl aromatic monomers is filtration through alumina. Another method of removing TBC from vinyl aromatic monomers is performed by washing the vinyl aromatic monomers with aqueous sodium or potassium hydroxide.

SUMMARY OF THE INVENTION

In one aspect, the present invention is a method for preparing a vinyl aromatic monomer. The method includes heating an admixture of the vinyl aromatic monomer and a 7-aryl-quinone methide wherein the 7-aryl-quinone methide is present at a concentration sufficient to prevent the vinyl aromatic monomer from polymerizing; separating the vinyl aromatic monomer and 7-aryl-quinonemethide methide to produce an overhead vinyl aromatic monomer distillate at a concentration sufficient to prevent the vinyl aromatic monomer from polymerizing; wherein the 4-tert-butylcatechol is introduced into the distillate such that essentially no 4-tert-butylcatechol enters the bottoms materials.

In another aspect, the present invention is a method for reworking a vinyl aromatic monomer and 4-tert-butylcatechol admixture in a process for preparing a vinyl aromatic monomer using a 7-aryl-quinone methide as a polymerization inhibitor. The method includes removing substantially all of the 4-tert-butylcatechol from the vinyl aromatic monomer and 4-tert-butylcatechol admixture prior to the vinyl aromatic monomer and 4-tert-butylcatechol admixture coming into contact with the vinyl aromatic monomer stabilized using a 7-aryl-quinone methide.

Another aspect of the present invention is a method for the in-situ deactivation of a selected polymerization inhibitor in a vinyl aromatic monomer. The method includes admixing: (A) an admixture of a vinyl aromatic monomer and a polymerization inhibitor selected from the group consisting of 4-tert-butylcatecholand a 7-aryl-quinone methide, and (B) a compound selected from the group consisting of 4-tert-butylcatechol and a 7-aryl-quinone methide; wherein the polymerization inhibitor of (A) is not the same as the compound of (B), and the ratio of the polymerization inhibitor of (A) and the compound of (B) is such that polymerization of the vinyl aromatic monomer is substantially not inhibited.

In still another aspect, the present invention is a method for preparing vinyl aromatic monomers. This method includes heating a vinyl aromatic monomer in the presence of a 7-aryl-quinone methide polymerization inhibitor and a 4-tert-butylcatechol polymerization inhibitor and further includes also using at least one other polymerization inhibitor wherein the at least one other polymerization inhibitor is present in an amount effective to prevent polymerization of the vinyl aromatic monomer and is not a hydroxylamine.

Another aspect of the present invention is a vinyl aromatic polymer prepared from a formulation including an unstabilized vinyl aromatic monomer, 4-tert-butylcatechol, and a 7-aryl-quinone methide.

DETAILED DESCRIPTION OF THE PREFERRED EMBODIMENTS

In one aspect, the present invention is a process improvement in a process for preparing a vinyl aromatic monomer wherein a 7-aryl-quinone methide is used in the process in an amount effective to inhibit polymerization of vinyl aromatic monomers. For purposes of the present invention, the 7-aryl-quinone-methidesare defined as those compounds having the general formula:

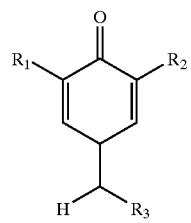

wherein $R_1$ and $R_2$ are independently H, $C_4$ to $C_{18}$ alkyl; $C_5$ to $C_{12}$ cycloalkyl; or $C_7$ to $C_{15}$ phenylalkyl. Preferably, $R_1$ and $R_2$ are tert-butyl, tert-amyl, tert-octyl, cyclohexyl, α-methylbenzyl or α,α-dimethylbenzyl. $R_3$ is preferably aryl, or aryl substituted with $C_1$ to $C_6$ alkyl, alkoxy, hydroxy, nitro, amino, carboxy, or mixtures thereof. Methods for preparing these compounds may be found in U.S. Pat. No. 4,032,547, which is hereby incorporated by reference. Most preferably, the 7-aryl-quinone methide is 2,6-di-tert-butyl-4-benzylidene-cyclo-2,5-dienone.

An important aspect of the present invention is the discovery of the fact that the two polymerization inhibitors, the 7-aryl-quinone methides and TBC, when used in combination, do not inhibit polymerization to the same extent as each would if used separately. Stated another way, a phenomenon has been observed that when these two compounds are used together, they can, to a large extent, render each other unable to inhibit polymerization in a vinyl aromatic monomer.

In processes for preparing vinyl aromatic monomers, it is commonly practiced to use polymerization inhibitors in the process to stabilize the monomer as it is produced. At certain critical parts of the process, an intermediate material comprising monomer, contaminants, and a polymerization inhibitor is subjected to heating to distill the comparatively low boiling monomer, producing a distillate that is primarily monomer and a bottoms material that includes monomer, polymerized monomer, and by-product contaminants. It is common at this point in the process to add TBC to the monomer distillate, typically at some location in the distillation unit, to prevent polymer formation.

A comparatively small amount of TBC can reduce a comparatively large amount of 7-aryl-quinone methide ineffective in inhibiting polymerization. If a vinyl aromatic monomer production process is using a 7-aryl-quinone methide as the process inhibitor and TBC is added to a distillation unit in that process at a location such that some of the TBC is allowed to reenter the process and collect in the bottoms material, then the bottoms material can begin to polymerize and rapidly increase in viscosity. These bottoms materials are usually discarded, often by burning. If the bottoms material increases in viscosity to the point of solidification or even just to the point that it cannot be easily pumped or otherwise removed for disposal, then process interruptions or even unit shutdowns can occur. The cost of unexpectedly shutting down a production facility due to a problem such as this can easily exceed $1,000,000.00 in clean out costs and lost production.

It would be desirable in the art of producing vinyl aromatic monomers to avoid expensive shutdowns due to undesired interactions between 7-aryl-quinone methides and TBC. Therefore, in one aspect, the present invention is a process improvement in a process for preparing a vinyl aromatic monomer wherein a 7-aryl-quinone methide is used in the process in an amount effective to prevent heated vinyl aromatic monomer from polymerizing and TBC is added to a vinyl aromatic monomer distillate in an amount effective to prevent polymerization of the vinyl aromatic monomer distillate, the improvement comprising preventing TBC from entering the process at any point wherein the vinyl aromatic monomer is stabilized by the 7-aryl-quinone methide. Note that the heating steps and the distillation steps of the method of the present invention can occur in the same or different parts of the process.

In one embodiment of the present invention, where the process for preparing a vinyl aromatic monomer includes a distillation column, TBC would not be added to the vinyl aromatic monomer distillate until the vinyl aromatic monomer distillate had exited the distillation column. An advantage of this embodiment is that TBC can be substantially excluded from the rest of the process, but delaying adding the TBC until this point in the process could result in excessive polymer formation.

In another embodiment of the present invention, where the process for preparing a vinyl aromatic monomer includes a distillation column, TBC is added within the column, but downstream from a separate recycle system which would prevent substantially all of the TBC from reaching the distillation bottoms. An advantage of this embodiment would be lower polymer production because the monomer would spend less time unmixed with a polymerization inhibitor. A disadvantage to such a system would be greater capitalization costs.

In a process of the present invention, wherein TBC is introduced into a vinyl aromatic distillate such that essentially no TBC enters the distillation bottoms, the TBC concentration in the distillation bottoms is less than 10 ppm, preferably less than 5 ppm, and most preferably less than 1 ppm. Any method known to be useful to those of ordinary skill in the art of preparing vinyl aromatic monomers for adding an effective amount of TBC to an aromatic monomer distillate prior to undesirable quantities of polymer forming but without also resulting in TBC entering the distillation bottoms can be used with the method of the present invention.

TBC is a preferred polymerization inhibitor for use with vinyl aromatic monomers being stored. Occasionally, a vinyl aromatic monomer in storage will not meet a specification or for some other reason not be in a condition to be sold. It is common in the field of preparing vinyl aromatic monomers to "rework" such off specification materials. For the purposes of the present invention, to rework a material means to recycle it into a production process such that the material is purified or otherwise returned to the desired specifications. Clearly, reworking a material that includes a TBC polymerization inhibitor into a process that uses a 7-aryl-quinone methide as a polymerization inhibitor may not be desirable. Therefore, another aspect of the present invention is a method for reworking a vinyl aromatic monomer stabilized using an effective amount of TBC in a process wherein a 7-aryl-quinone methide is used in the process in an amount effective to prevent vinyl aromatic monomer from polymerizing, the improvement including removing the TBC from the vinyl aromatic monomer to be reworked before the vinyl aromatic monomer to be reworked comes into contact with vinyl aromatic monomer stabilized using a 7-aryl-quinone methide.

Any method useful for removing TBC from a vinyl aromatic monomer known to those of ordinary skill in the art of preparing such vinyl aromatic monomers can be used with the present invention. For example, washing with an aqueous base can be used as can filtering through alumina.

Another method which can be used to avoid shutting down a vinyl aromatic monomer production plant due to an undesirable interaction of TBC and a 7-aryl-quinone methide would be to use at least one additional polymerization inhibitor in the process in a concentration such that the additional inhibitor would be present in distillation bottoms in an amount effective to prevent the rapid polymerization of bottoms materials. Such a solution would prevent the rapid increase in viscosity bottoms and polymer formation in monomer that could cause a shut down, but would also require the sacrifice of at least some of the benefits of using a 7-aryl-quinone methide alone.

The absence or low occurrence of heteroatoms such as nitrogen and halogens in the preferred 7-aryl-quinone methides could be desirable from a perspective of disposing of the bottoms materials. Particularly when the desired method of disposal is burning for fuel, the necessity of reducing the discharge of compounds such as $NO_x$ and the like can greatly increase the cost of such disposal practices. The use of low nitrogen and halogen or nitrogen and halogen free polymerization inhibitors reduce or eliminate these costs.

Additional polymerization inhibitors that could be used with the method of the present invention include: phenothiazine, 2,6-dinitro-p-cresol, 2-sec-butyl-4,6-dinitrophenol, and other phenols and poly-hydroxy aromatics such as hydroquinone and hydroquinone monomethyl ether; aromatic amines such as N,N'-di-2-naphthyl-p-phenylenediamine, N-phenyl-N'-(1,3-dimethylbutyl)-p-phenylenediamine,and N,N'-diphenyl-p-phenylenedia disclosed in U.S. Pat. No. 6,348,598, which is hereby incorporated by reference. Any composition that is suitable as a polymerization inhibitor for use with vinyl aromatic monomers, except as otherwise noted herein, can be used with the method of the present invention.

It is intended that the present invention can be used in the production and storage of any vinyl aromatic monomers. Exemplary of such monomers are monomeric styrene and alpha-methyl styrene. The present invention is particularly directed to styrene production and storage.

Another embodiment of the present invention is a method for the in-situ deactivation of a selected polymerization inhibitor in a vinyl aromatic monomer comprising admixing: (A) an admixture of a vinyl aromatic monomer and a polymerization inhibitor selected from the group consisting of TBC and a 7-aryl-quinone methide, and (B) a compound selected from the group consisting of TBC and a 7-aryl-quinone methide; wherein the polymerization inhibitor of (A) is not the same as the compound of (B). Prior to polymerization, it is often desirable to remove a polymerization inhibitor from a vinyl aromatic monomer. Rather than using the prior art methods described above, that is distillation, caustic washes, and filtration, the effect of one polymerization inhibitor can be negated by an addition of an effective amount of the other polymerization inhibitor. Stated another way, if the monomer is stabilized with TBC, then an addition of a 7-aryl-quinone methide can be used to overcome the stabilizing effects of the TBC.

Of TBC and the 7-aryl-quinone methides, TBC is more effective, by weight, at nullifying the ability of a 7-aryl-quinone methide to inhibit polymerization of a vinyl aromatic monomer. For example, a styrene monomer including from 15 to 30 parts per million (ppm) TBC and 100 ppm of a 7-aryl-quinonemethide will form polymer at about the same rate as the same monomer having no polymerization inhibitor present. The effectiveness of TBC for polymerization stabilization is well known and 7-aryl-quinone methide is about as effective as, for example, 2,6-dinitro-p-cresol. The ratio of 7-aryl-quinonemethide to TBC necessary to substantially remove the ability of the two materials to stabilize a vinyl aromatic monomer is from about 3:1 to about 40:1, preferably about 4:1 to 25:1, and most vinyl aromatic monomers comprising heating a vinyl aromatic monomer in the presence of a 7-aryl-quinone methide polymerization inhibitor and a 4-tert-butylcatechol polymerization inhibitor and further comprising also using at least one other polymerization inhibitor wherein the at least one other polymerization inhibitor is present in an amount effective to prevent polymerization of the vinyl aromatic monomer and is not a hydroxylamine. The hydroxylamines excluded from the combinations of polymerization inhibitors of the present invention have the general formula:

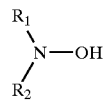

wherein $R_1$ and $R_2$ are the same or different and are hydrogen, alkyl, aryl, alkaryl, aralkyl, or hydroxyalkyl groups and preferably have about three to about twenty carbon atoms. Any other combination of a 7-aryl-quinone methide and a polymerization inhibitor is intended to be within the scope of the present invention. The polymerization inhibitors can be admixed with the stabilized monomer using any method known to those of ordinary skill in the art of preparing vinyl aromatic monomers or polymers to be useful in admixing such materials.

Another embodiment of the present invention is a vinyl aromatic polymer prepared from a formulation including an unstabilized vinyl aromatic monomer, TBC, and a 7-aryl-quinone methide. Preferably, the TBC is present at a concentration in the polymer of from about 10 to about 30 ppm. Also preferably, the 7-aryl-quinone methide is present within the ratios already disclosed and at a level sufficient to render the TBC in effective at inhibiting polymerization, or at a concentration of from about 30 ppm to about 240 ppm.

EXAMPLES

The following examples are provided to illustrate the present invention. The examples are not intended to limit the scope of the present invention and they should not be so interpreted. Amounts are in weight parts or weight percentages unless otherwise indicated.

Example 1

A flask test of the effectiveness of 2,6-di-tert-butyl-4-benzylidene-cyclo-2,5-dienone is performed by admixing 100 ppm by weight of 2,6-di-tert-butyl-4-benzylidene-cyclo-2,5-dienone with styrene monomer at a temperature of about 122° C. in the absence of oxygen. After 90 minutes, a sample of the styrene monomer is tested for polymer content using methanol precipitation. The polymer content is determined to be 2.5 percent.

Example 2

Example 1 is repeated and tested substantially identically except that the admixture of 2,6-di-tert-butyl-4-benzylidene-cyclo-2,5-dienone and styrene monomer additionally includes 15 ppm 4-tert-butylcatechol. The polymer content is determined to be 10 percent.

Example 3

Example 1 is repeated and tested substantially identically except 100 ppm of phenylenediamine is additionally admixed with the monomer. Note that the lack of oxygen prevents the phenylenediamine from acting as polymerization inhibitor. The polymer content is determined to be 2 percent.

Example 4

A flask test is performed using a styrene monomer containing 15 ppm 4-tert-butylcatechol which is admixed with 100 ppm phenylenediamine and 100 ppm 2-sec-butyl-4,6-dinitrophenol. The monomer admixture is heated at 122° C.

in the absence of oxygen for 2 hours. A sample of the admixture is taken and analyzed for polymer content. Note that the lack of oxygen prevents the phenylenediamine from acting as polymerization inhibitor. The polymer content is determined to be 2 percent.

Example 5

A flask test is performed and tested substantially identically to Example 4 except that 2,6-di-tert-butyl-4-benzylidene-cyclo-2,5-dienone is used instead of 2-sec-butyl-4,6-dinitrophenol. The polymer content is determined to be about 6 percent.

Example 6

A flask test is performed and tested substantially identically to Example 4 except that no polymerization inhibitor is used. The polymer content is determined to be about 13 percent.

Example 1 shows the extent of polymer formation in a 2,6-di-tert-butyl-4-benzylidene-cyclo-2,5-dienone inhibited monomer. Example 2 shows that addition of 4-tert-butylcatechol to the same monomer increases polymer formation. Example 3 shows that adding phenylenediamine to a 2,6-di-tert-butyl-4-benzylidene-cyclo-2,5-dienone inhibited monomer does not cause an increase in polymer formation, even in the absence of oxygen which is required by the phenylenediamine to act as a polymerization inhibitor. Example 4 shows that the effect of adding both 4-tert-butylcatechol and phenylenediamine, which both require oxygen to act as polymerization inhibitors, to 2-sec-butyl-4,6-dinitrophenol does not increase polymer formation. Example 5 shows that repeating Example 4 where 2,6-di-tert-butyl-4-benzylidene-cyclo-2,5-dienone is used instead of 2-sec-butyl-4,6-dinitrophenol results in increased polymer formation. Example 6 shows the extent of polymer formation in an uninhibited system.

What is claimed is:

1. A method for preparing a vinyl aromatic monomer comprising: heating an admixture of the vinyl aromatic monomer and a 7-aryl-quinone methide wherein the 7-aryl-quinone methide is present at a concentration sufficient to prevent the vinyl aromatic monomer from polymerizing; separating the vinyl aromatic monomer and 7-aryl-quinone methide to produce an overhead vinyl aromatic monomer distillate and a bottoms material; and introducing 4-tert-butylcatechol into the distillate at a concentration sufficient to prevent the vinyl aromatic monomer from polymerizing; wherein the 4-tert-butylcatechol is introduced into the distillate such that essentially no 4-tert-butylcatechol enters the bottoms materials.

2. The method of claim 1 wherein the vinyl aromatic monomer is styrene.

3. The method of claim 2 wherein the 7-aryl-quinone methide is 2,6-di-tert-butyl-4-benzylidene-cyclohexa-2,5-dienone.

4. The method of claim 3 wherein the separation is performed by distillation using a distillation column which produces the styrene monomer distillate and a distillation bottoms.

5. The method of claim 4 wherein the 4-tert-butylcatechol is introduced into the vinyl aromatic monomer distillate at a point after the vinyl aromatic monomer distillate has exited the distillation column.

6. The method of claim 4 wherein the distillation column has a column recycle system which collects substantially all of the material returning to the distillation column bottoms.

7. The method of claim 6 wherein the 4-tert-butylcatechol is introduced into the vinyl aromatic monomer distillate at a point downstream from the column recycle system.

8. The method of claim 4 wherein the distillation bottoms have a 4-tert-butylcatechol content of less than 10 ppm.

9. The method of claim 4 wherein the distillation bottoms have a 4-tert-butylcatechol content of less than 1 ppm.

* * * * *